US000001430H

United States Statutory Invention Registration [19]

[11] Reg. Number: H1430

Apel et al.

[43] Published: Apr. 4, 1995

[54] CLAY ENHANCEMENT OF METHANE, LOW MOLECULAR WEIGHT HYDROCARBON AND HALOCARBON CONVERSION BY METHANOTROPHIC BACTERIA

[75] Inventors: William A. Apel; Patrick R. Dugan, both of Idaho Falls, Id.

[73] Assignee: The United States of America as represented by the United States Department of Energy, Washington, D.C.

[21] Appl. No.: 738,001

[22] Filed: Jul. 30, 1991

[51] Int. Cl.[6] ..... C12M 1/14; C12M 1/04

[52] U.S. Cl. ..... 435/310; 435/313

[58] Field of Search ..... 435/266, 176, 252.1, 435/262.5, 313, 858

[56] References Cited

U.S. PATENT DOCUMENTS 4,348,476 9/1982 Hou ..... 435/313

FOREIGN PATENT DOCUMENTS 2219621 12/1989 United Kingdom ..... 435/266

OTHER PUBLICATIONS

Arvin, E. "Biodegradation Kinetics of Chlorinated Aliphatic Hydrocarbons . . . " Water Research 25(7) 1991 from Biosis BA92:63521.

T. L. Weaver et al., "The Eutrophication Implications of Interactions Between Naturally Occurring Particulates and Methane Oxidizing Bacteria", Water Research Pergamon Press 1972, pp. 817–828.

T. L. Weaver et al., "Enhancement of Bacterial Methane Oxidation by Clay Minerals", Reprinted from Nature, vol. 237, No. 5327, p. 518, Jun. 30, 1972.

P. R. Dugan et al., "Degradation of Trichloroethylene by Methane Oxidizing Bacteria Grown in Liquid or Gas/Vapor Phase", The Winter Annual Meeting of the Amer. Soc. of Mech. Engineers, Dallas, Tex., Nov. 25–30, 1990, pp. 55–59.

William A. Apel et al., "Use of Methanotrophic Bacteria in Gas Phase Bioreactors to Abate Methane in Coal Mine Atmospheres", American Chemical Society, vol. 35, No. 3, pp. 943–950.

*Primary Examiner*—Shean Wu

*Attorney, Agent, or Firm*—James W. Weinberger; John M. Albrecht; William R. Moser

[57] ABSTRACT

An apparatus and method for increasing the rate of oxidation of toxic vapors by methanotrophic bacteria. The toxic vapors of interest are methane and trichloroethylene. The apparatus includes a gas phase bioreactor within a closed loop pumping system or a single pass system. The methanotrophic bacteria include *Methylomonas methanica, Methylosinus trichosporium,* and uncharacterized environmental enrichments.

2 Claims, 6 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

CLAY ENHANCEMENT OF METHANE, LOW MOLECULAR WEIGHT HYDROCARBON AND HALOCARBON CONVERSION BY METHANOTROPHIC BACTERIA

CONTRACTUAL ORIGIN OF THE INVENTION

The U.S. Government has rights in this invention pursuant to Contract No. DE-AC07-76ID01570 between the U.S. Department of Energy and EG&G Idaho, Inc.

FIELD OF THE INVENTION

The invention relates to a combined system of an apparatus and a method of increasing the rates of oxidation of gases and hazardous vapors by methanotrophic and other bacteria. The gases of interest are methane and trichloroethylene and other hazardous vapors. In a preferred embodiment, the oxidation rate of methane is improved by the addition of clays, e.g., kaolin, sometimes called "China clay".

BACKGROUND OF THE INVENTION

Methane ($CH_4$) is an asphyxiant gas that is colorless, odorless, tasteless, and lighter than air. It is practically inert toward sulfuric acid, nitric acid, alkalies, and salts but reacts with chlorine and bromine in light (explosively in direct sunlight). It is soluble in alcohol and ether but only slightly soluble in water. Methane occurs in natural gas and coal gas and from decaying vegetation and other organic matter in swamps and marshes.

Trichloroethylene ($CHCl{:}CCl_2$) is a stable, low-boiling, colorless, photoreactive liquid having a chloroform-like odor. It will not attack the common metals even in the presence of moisture. It is miscible with common organic solvents and slightly soluble in water. It is used as a metal degreaser; an extraction solvent for oils, fats, and waxes; a solvent dye; dry cleaning fluid; as well as a refrigerant and heat exchange liquid. It also is used for cleaning and drying electronic parts. The vapor is toxic by inhalation and use as a solvent is not permitted in some states. The FDA has prohibited its use in foods, drugs, and cosmetics.

Methanotrophic bacteria, those that oxidize methane, have been known and studied for the past 85 years. During this period, the basic physiological capabilities of these organisms have been elucidated with their ability to sequentially oxidize methane, in the presence of air, to carbon dioxide and water, being particularly well defined.

In recent years, increased emphasis has been placed on exploiting the physiological potential of the methanotrophs. Areas of interest include bioconversion of methane to alternate and potentially valuable products, such as methyl alcohol, methyl ketones, and formaldehyde, etc., control of methane in coal mine atmospheres, and degradation of environmentally significant low-molecular weight halocarbons like trichloroethylene in liquid and vapor phases. As a result of these interests, development of bioreactor systems allowing more efficient conversion of gases and vapors are of considerable relevance.

Traditionally, production of large amounts of methanotrophic bacteria, as would be required for the above applications, has been accomplished by growing the organisms on methane/air mixtures that are then added to liquid cultures. An inherent limitation of this method is the relatively limited transfer of methane and air to the liquid phase, since the solubility of methane in water is very low. Consequently, these gases are not available to the bacteria in sufficient quantity and, therefore, become rate limiting. Various techniques have been employed to combat this problem including mechanical agitation and sparging of methane/oxygen or methane/air mixtures through the cultures in an attempt to saturate the liquid culture medium with the necessary gases.

One approach to increasing gas delivery to the methanotrophic bacteria is culturing the organisms on inert supports suspended in a gas or vapor phase. In such a system, gas and/or vapor availability to the cells can be increased. As such, it should be theoretically possible to increase methanotrophic gas and vapor removal rates by making the necessary gases or vapors more readily available to the organisms.

Methods to increase rates of $CH_4$ oxidation by methanotrophic bacteria are of interest for the bioconversion of $CH_4$ to alternate compounds and for controlling $CH_4$ levels, for instance, in mine atmospheres. The rate of $CH_4$ conversion per unit weight of *Methylomonas methanica* cells has been shown to be higher in gas phase bioreactors than in liquid cultures. Additionally, the effects of kaolin on $CH_4$ oxidation rates by *Methylomonas methanica* in both liquid cultures and gas phase bioreactors has been shown experimentally.

Kaolin (China clay) is a white-burning aluminum silicate which, due to its great purity, has a high fusion point and is the most refractory of all clays. It is composed of alumina ($Al_2O_3$) and silica ($SiO_2$).

It is the purpose of this invention to demonstrate the improvement in the oxidation rate of methane by *Methylomonas methanica* by the addition of kaolin clay to the apparatus.

It is a further purpose of this invention to demonstrate an apparatus that reduces the concentration of trichloroethylene vapor in a gas by cultures of specific methanotrophic bacteria.

SUMMARY OF THE INVENTION

The invention simply stated comprises: a bioreactor container having within it a number of microbial carrier means, such as Pall rings, ceramic bio-rings, or fibrous supports, etc. The bacteria are grown on the bio-rings and then a gas containing a hazardous vapor is circulated through a closed loop conduit means or tubing by a gas pump, through a humidifying salt solution and up through the bio-reactor. Reduction in either gas Or hazardous vapor is measured by a gas chromatograph at a gas sample means in a tubing section adjacent the pump.

In a first experiment, the microorganism, *Methylomonas methanica* is used to determine the rates of oxidation of methane in both a liquid culture and gas phase bioreactor experiment.

In a further experiment, *Methylomonas methanica* is used in conjunction with the kaolin clay demonstrating an improved oxidation rate of methane.

A process for removing the toxic vapor from the gas generally stated includes the steps of: growing microorganisms, e.g., methanotrophic bacteria, on a carrier means within a bioreactor, filling a lower portion of the bioreactor with a salt solution and then pumping the gas within a closed loop through the salt solution and methanotrophic bacteria culture, thereby oxidizing and decreasing the hazardous vapor concentration. Although the process described herein generally discloses a recirculatory system, it has been demonstrated, by varying the parameters, that a single pass process is also effective.

Other objects, advantages, and capabilities of the present invention will become more apparent as the description proceeds.

DETAILED DESCRIPTION OF THE INVENTION

Figure 1:
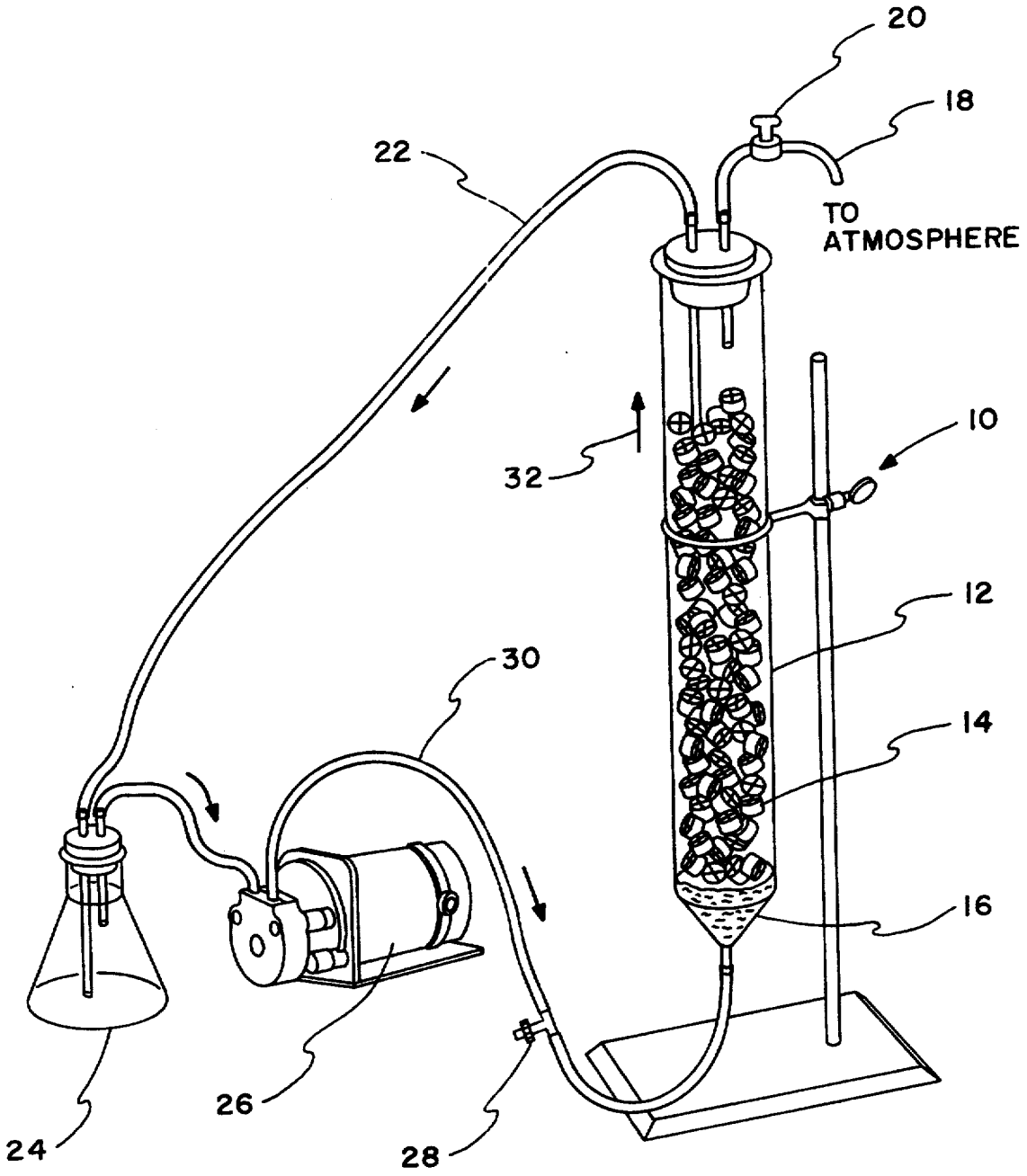
FIG. 1 is a schematic diagram of a gas phase bioreactor of the present invention.

Referring to FIG. 1, a preferred apparatus 10 for removal of toxic vapors from a gas is disclosed. A bioreactor container 12 has been filled with carrier means (Pall rings) 14 that have been coated with a culture of methanotrophic bacteria by allowing the bacteria to grow on the Pall rings. A lower portion of the bioreactor container contains a humidifying salt solution 16. An optional purge line 18 and purge valve 20; and a first conduit means, e.g. Teflon TM tubing 22, connects to an optional gas flask 24 and pump 26. Sample drain and fill valve 28 is installed in a second conduit or tubing 30 forming a closed loop. This apparatus was used for experiments on methane concentration reduction.

Figure 5:
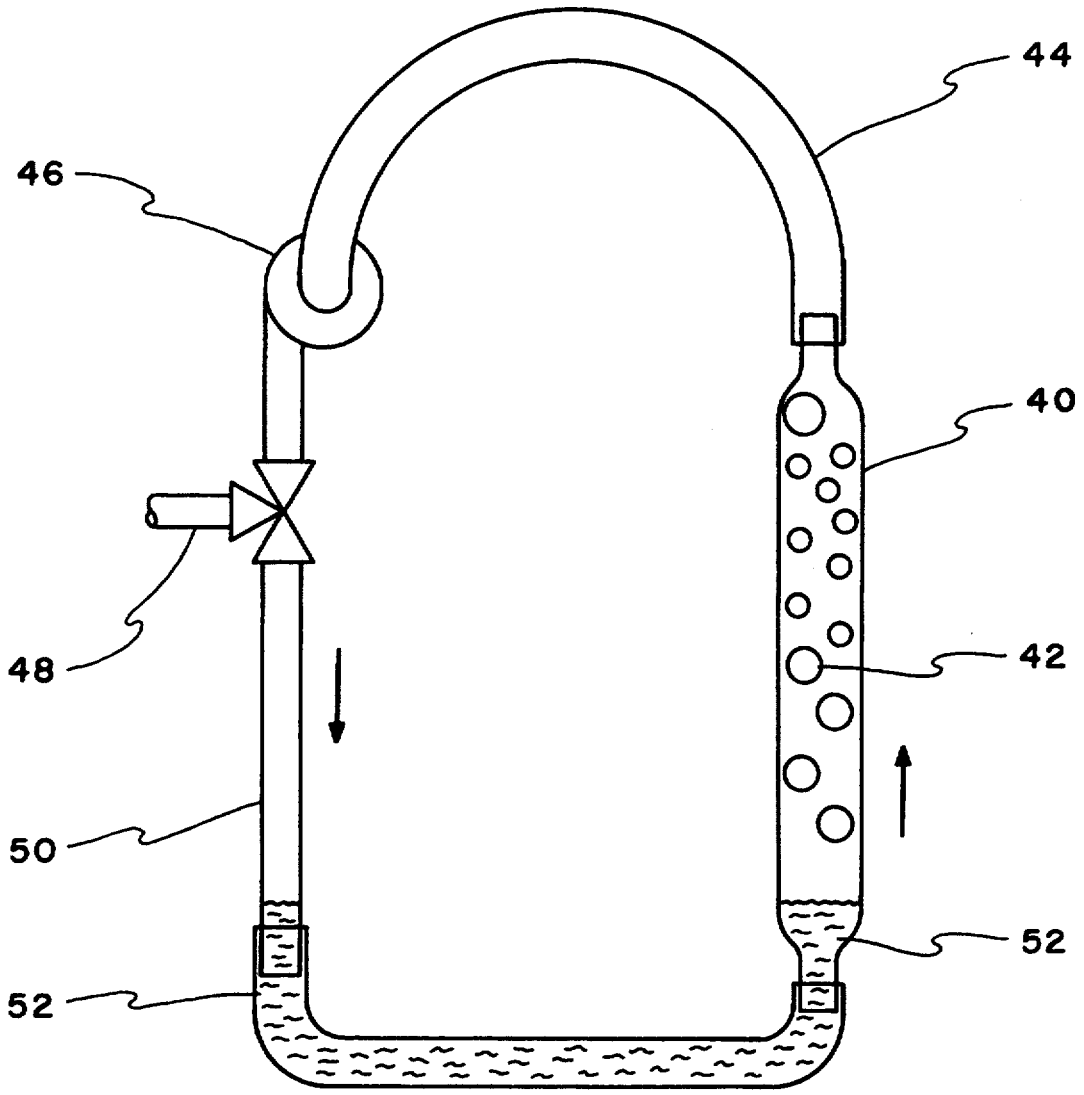
FIG. 5 is a schematic diagram of a gas phase bioreactor for removal of trichloroethylene (TCE)
Figure 6:
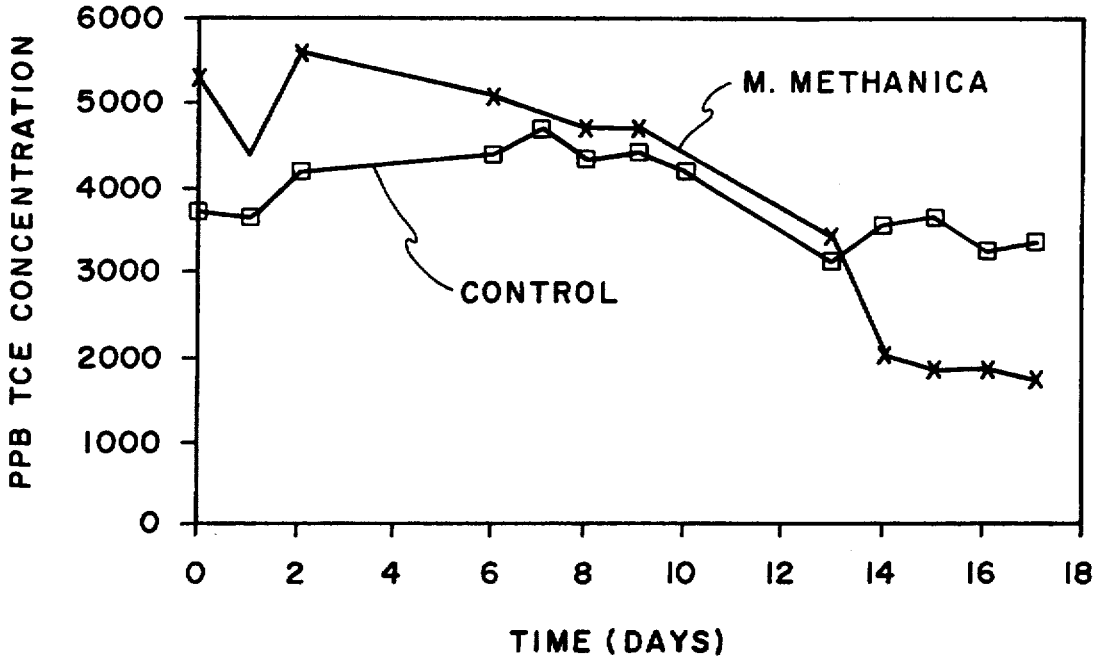
FIG. 6 is a graph of TCE concentration versus time.

A second similar apparatus used for trichloroethylene reduction is illustrated in FIG. 5. It consists of bioreactor container 40 having the coated carrier means or biorings 42 within. The closed loop consists of tubing, pump 46, sample valve 48, pump discharge tubing 50, and salt solution 52.

Operation of these apparatus will be described in the following experiment descriptions.

Experiment No. 1—Enhanced Methane Oxidation Rates by Methanotrophic Bacterium, *Methylomonas methanica*, Grown in Bioreactors This experiment was performed to determine which method of methane oxidation by *Methylomonas methanica* has the higher oxidation rate, i.e., gas phase bioreactors (present invention) or shaken liquid phase methods (i.e., the prior art).

The strain of *Methylomonas methanica* used in these experiments was O.S.U. 739 which was provided by the Ohio State University, Department of Microbiology (Columbus, Ohio, U.S.A.). Cultures were maintained in CM salts medium. CM salts solution contained the following (g/L): $KNO_3$ 1.00; Mg $SO_4.7H_2O$, 0.02; $CaCl_2$, 0.02; $FeSO_4.7H_29$, 0.01; $NaHPO_4$, 0.23; $NaH_2PO_4.H_2O$, 0.07; $H_3BO_4$, trace; $MnSo_4$, trace; $ZnSO_4$, trace; $MoO_3$, trace. All liquid culture methane depletion studies were performed using *Methylomonas methanica* at stationary phase in the liquid cultures as described above for culture maintenance. During these studies, the cultures were incubated at 22±2° C. in sealed serum bottles held in an inverted position on a gyratory shaker set at 120 rpm.

The gas phase bioreactors were constructed by filling a 3×30 inch glass column 12 with ⅝ inch Pall rings 14 (Norton Chemical, Process Products Division, Akron, Ohio, U.S.A.) and sealing the open end with a rubber stopper. The seal was further secured by over-wrapping the boundary area between the stopper and the column with parafilm. A closed loop for gas recirculation through the bioreactor was constructed using flexible 5/32 inch o.d. Teflon TM tubing connected to the upper and lower ends of the bioreactor. Included in the loop was a one-liter Erlenmeyer flask 24 to increase the gas volume of the system and a peristaltic pump 26 to recirculate the gas. The gas was circulated in an up-flow direction through the bioreactor at a rate of 200 cc/min as at arrow 32. Approximately 100 ml of CM salts medium 16 was maintained in the base of the bioreactor to humidify the recirculating gas mixture. Total system volume was measured by water displacement and found to be 4.5 Liters.

The gas phase bioreactors were inoculated with *Methylomonas methanica* and incubated until the bioreactors reached steady state methane-oxygen uptake and carbon dioxide evolution. This occurred approximately 6 weeks after inoculation at a methane uptake rate of 40 mg methane/hr when feeding the bioreactors a 30% methane air-gas mixture. This rate was maintained for several months by occasionally draining the humidification heel 16 of CM salts medium from the base of the bioreactors and trickling 100 ml of fresh, sterile, CM salts medium over the Pall ring supports. The fresh CM salts solution was allowed to collect as a new humidification heel in the bottom of the reaction. Methanotrophic bacteria grew in this heel, but studies demonstrated no significant measurable methane uptake could be attributed to these organisms versus those growing on the supports in the gas phase. All methane uptake rate studies were performed in the steady-state gas phase bioreactors at 22±2° C. For methane depletion studies, both the liquid cultures and the gas phase bioreactors were charged with various concentrations of methane in air. Methane, oxygen, and carbon dioxide levels were monitored in the gas phase bioreactors and in the head space of the liquid cultures using a chromatographic method. Rates of methane uptake-per-unit of biomass-per-unit-time were calculated from these data.

Figure 2:
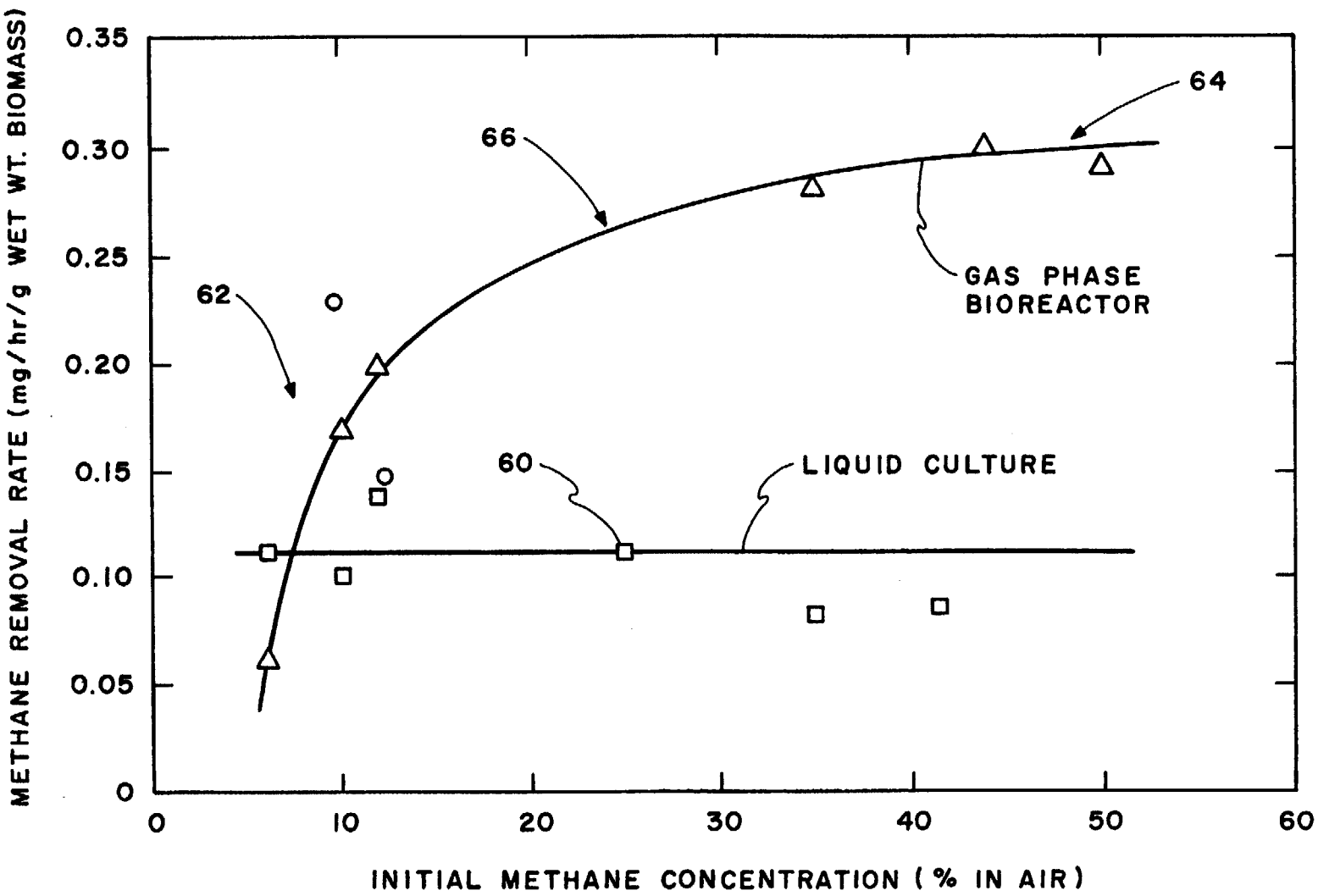
FIG. 2 is a graph of methane removal rate versus initial methane concentrations.

A comparison of methane oxidation rates by *Methylomonas methanica* at various initial methane concentrations in liquid cultures and gas phase bioreactors is illustrated in FIG. 2. Over the methane-concentration range tested, methane removal rates remained relatively constant in the shaken liquid cultures at an average of approximately 0.11 mg of methane removed per hour per gram wet weight of biomass, as at line 60. At lower initial methane concentrations, the methane removal rates in the gas phase bioreactors increased as initial methane concentration increased, as indicated at 62. However, at higher initial methane concentrations, the methane removal rates plateaued and did not increase as a function of further increased methane concentration, as indicated at 64.

These data strongly imply that under the experimental conditions employed in these studies, methane availability to the bacteria cells is a limiting factor at lower initial methane concentrations in the gas phase bioreactors. Analysis of gas concentration data from the gas phase bioreactors shows at higher initial methane concentrations exceeding approximately 10% to 15% methane, as indicated at 66, in air, $O_2$ availability appears to be a primary rate limiting factor. It has been shown that the process is effective in the range from about 1% to 50% methane.

In the liquid cultures over the methane-concentration ranges tested, it appears methane solubility in the culture medium, and, hence, its availability to the cells, may be the limiting factor. Regardless, it is evident that methane removal rate in the gas phase bioreactors running under high methane conditions was approximately three-fold greater than the average methane removal rates observed with the liquid cultures over the methane concentration range tested.

Experiment No. 2—The Stimulatory Effects of Kaolin on Methane ($CH_4$) oxidation by *Methylomonas methanica* in Liquid culture and Gas Phase Bioreactors This experiment was performed to determine the effect of the addition of kaolin to *Methylomonas methanica* in liquid cultures and gas phase bioreactors on $CH_4$ oxidation rates by these bacteria.

Liquid Culture Studies

*Methylomonas methanica* was maintained in 50 ml aliquots of CM mineral salts medium contained in 125 ml serum bottles sealed with crimped Teflon TM -coated rubber septa. The bottles were gassed with 30% $CH_4$ in air and incubated at 22±2° C. in an inverted position on a rotary shaker. Gas levels were monitored via gas chromatography with the bottles being regassed upon depletion of either the $CH_4$ or $O_2$. The stock culture was transferred to fresh medium biweekly to maintain viability.

Effects of kaolin on $CH_4$ oxidation were evaluated by adding kaolin at 4% w/v to the serum bottles containing CM salts, adding a standard inoculum of *Methylomonas methanica*, gassing with 12% $CH_4$ in air and assaying $CH_4$, $CO_2$, and $O_2$ levels versus control cultures without kaolin.

Gas Phase Bioreactor Studies

The bench scale, methanotrophic, gas phase bioreactors 10 (GPBs) were constructed as previously described using a 3×30 inch glass column 12 filled with ⅜ inch Pall rings 14 as inert microbial supports (FIG. 1). The GPBs were inoculated with a 50 ml culture of stationary phase *Methylomonas methanica*. The GPBs were incubated at 20±2° C. for 6 weeks at targeted gas levels of 30% $CH_4$ in air. The gas mixture was constantly recirculated and periodically monitored via gas chromatography. The bioreactors were regassed to the above target levels whenever the $CH_4$ or $O_2$ fell below 5.0%. The rates of $CH_4$ and $O_2$ uptake and $CO_2$ evolution reached steady state in 6 weeks with approximately 133 grams wet weight of biomass per bioreactor. One GPB was then treated with kaolin by completely flooding the Pall rings with CM salts medium supplemented with 4% w/v kaolin. The mixture was circulated within the bioreactor for two hours, after which it was drained. A non-kaolin, control GPB was established by treating a second steady state bioreactor as described above except CM salts medium without kaolin was circulated. Experiments determining rates of gas depletion were performed by flushing the GPBs with air and then gassing with a known mixture of $CH_4$ in air which was recirculated through the bioreactor at 200 ml/min.

Analytical Methods $CH_4$, $O_2$, and $CO_2$ in the serum bottle cultures and the GPBs were analyzed using a Gow-Mac series 550P gas chromatograph with a thermal conductivity detector and an Alltech CTR1 column at 30° C. Helium was the carrier gas at a flow rate of 60 milliliters per minute.

Results

Figure 3:
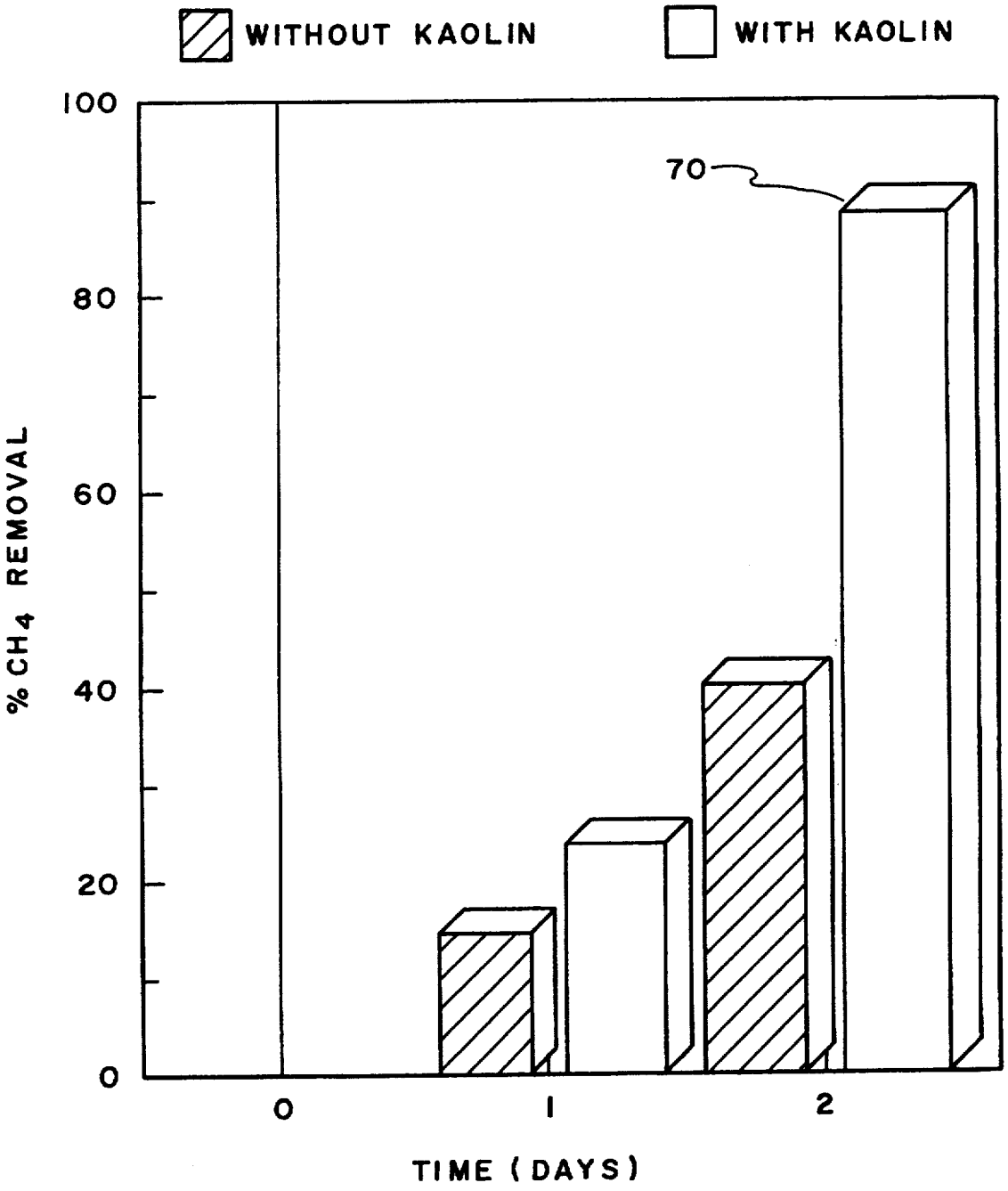
FIG. 3 is a bar chart of the percentage of methane removal rate versus time with and without kaolin.

Addition of kaolin increased $CH_4$ oxidation rates versus controls without kaolin. In liquid cultures at 20±2° C., addition of 4% w/v kaolin increased $CH_4$ oxidation rates (12% $CH_4$ in air) by *Methylomonas methanica* 2.4× to a rate of 0.14 mg $CH_4$ removed/hr/g wet cells, as seen in FIG. 3 at 70. Similarly, with *Methylomonas methanica* grown in gas phase bioreactors also at 20±2° C., a 1.4× increase in the $CH_4$ oxidation rate (10% $CH_4$ in air) to 0.23 mg methane removed/hr/g wet wt of cells was noted upon addition of kaolin.

Figure 4:
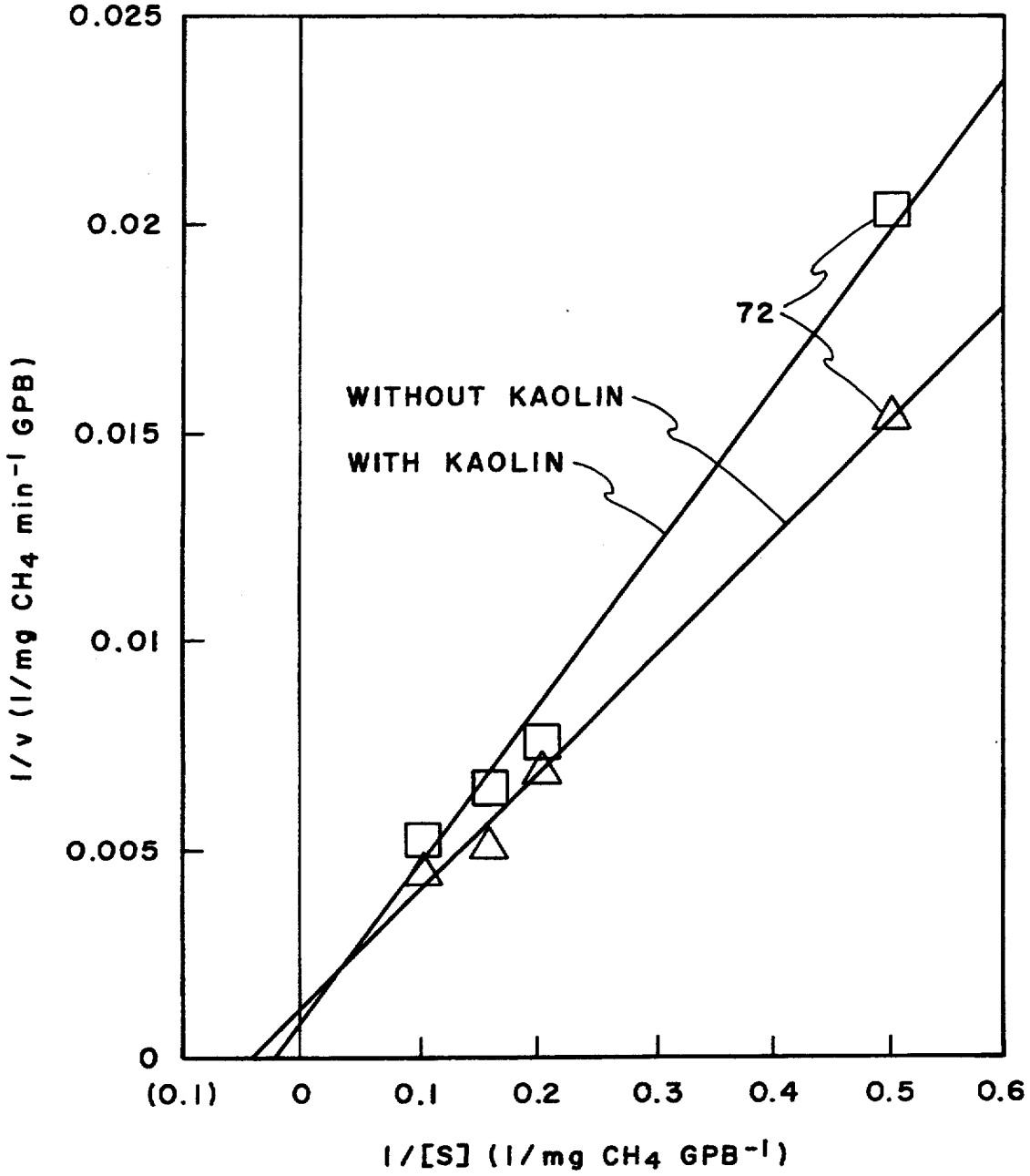
FIG. 4 is a graph of a reciprocal of removal rate versus a reciprocal of mass of methane.

This improvement in oxidation in the rate in the gas phase bioreactor due to kaolin addition is indicated at 72 of FIG. 4. It has been demonstrated that the kaolin range of 0.004% to 8% can be used.

Experiment No. 3—Degradation of Trichloroethylene in Gas Phase Bioreactors by Methanotrophic Bacteria This experiment was performed to determine if TCE vapors can be degraded in gas phase bioreactors by methanotropic bacteria.

Referring to FIG. 5, for the gas/vapor phase bioreactor experiment, two gas phase bioreactors were constructed using Kimax beaded process pipe (40) (7.6 cm i.d.×61 cm in length) with reducers (7.6 cm×5.1 cm) clamped to each end (from O-I/Schott, Process Systems, Inc., Vineland, N.J., U.S.A.). Teflon TM -coated rubber stoppers sealed off both ends of each column. Teflon TM tubing 44 and 50 (6.4 mm o.d.) connected from one end of the column to the other with a short segment of Masterflex tubing passing through a peristaltic pump 46 (Masterflex standard pump head 7016-20) set at a speed of 21 ml/min in order to circulate gas through the column. A sampling means 48 was constructed at the junction of the Teflon TM 50 and Masterflex tubing. PAO-1 was grown on 13 mm bio-rings 42 in one column. *Methylosinus trichosporium* was grown on 13 mm bio-rings in another column and *Methylomonas methanica* was grown on a third column. An uninoculated column was filled with 13 mm bio-rings and maintained as a control column. CM mineral salts (400 ml) was added to each column, as at 52. Copper was not added. The columns were sealed with silicone sealer and then were purged with 5% methane in air. The methane and oxygen were analyzed on the Gow-Mac gas chromatograph once per week. TCE was added through the sampling port 48 until a final concentration of 5 ppm was reached (87.5 ml of 200 ppm TCE). The TCE levels were measured on the Hewlett-Packard #5890A gas chromatograph with an electron capture detector (at 260° C.) and an Alltech 624 non-packed column. The injection temperature was 225° C., the carrier gas was helium at 5 ml per minute, and the auxiliary gas was nitrogen at 65 ml per minute. TCE and methane were analyzed daily by gas chromatography.

Results

Bioreactors

Figure 7:
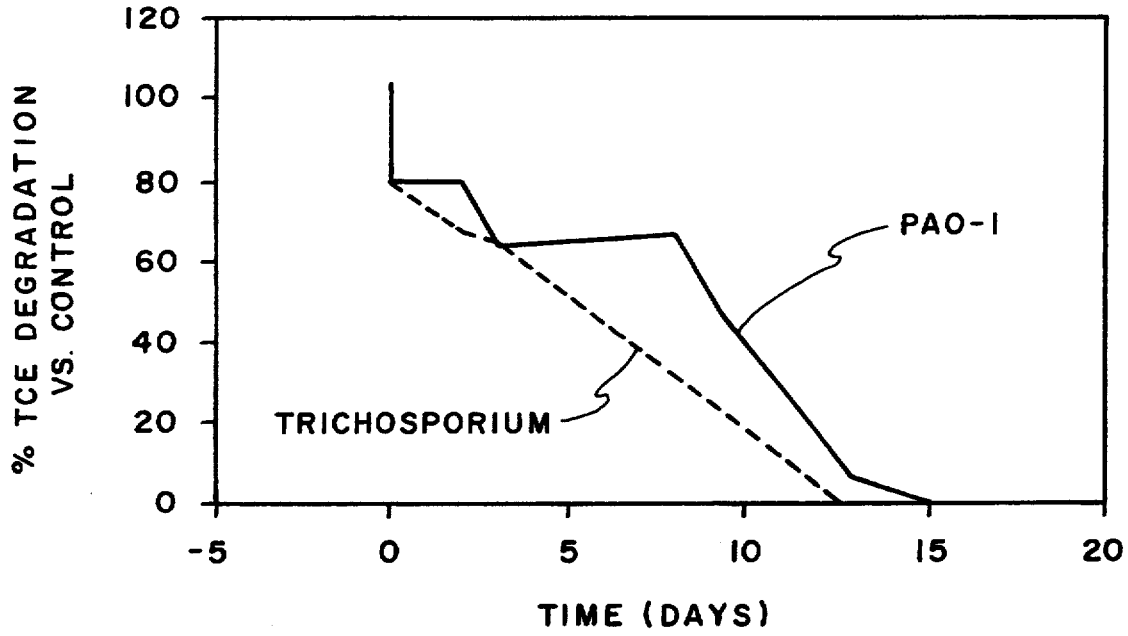
FIG. 7 is a graph of TCE concentration versus time corrected to account for surface adsorption.

When TCE was added to columns of *Methylomonas methanical, no degradation could be demonstrated although* $CH_4$ consumption was in excess of 38 mg $CH_4$ oxidized per hour. FIG. 7 presents a graph of TCE removed versus time after correction for surface adsorption. TCE was removed when the bacteria used in this gas phase bioreactor was either *Methylosinus trichosporium* or PAO-1.

While two embodiments of the invention have been disclosed, various modes of carrying out the principles disclosed herein are contemplated as being within the scope of the following claims. Therefore, it is understood that the scope of the invention is not to be limited except as otherwise set forth in the claims.

What is claimed is:

1. Apparatus for removal of a methane vapor within a gas comprising:

a. a bioreactor container closed to the atmosphere having a plurality of carrier means, said carrier means coated with a methanotrophic bacteria culture and a kaolin clay;

b. a conduit means connecting a bioreactor container outlet to a gas pump;

c. a second conduit means connecting the gas pump to a bioreactor container lower portion;

d. a gas sample means connecting to the second conduit means; and e. a humidifying salt solution within the bioreactor container lower portion, wherein the gas is circulated through the salt solution and carrier means by the gas pump so as to remove the methane vapor from the gas.

2. Apparatus for removal of a methane vapor within a gas comprising:

a. bioreactor container closed to the atmosphere having a plurality of carrier rings, said carrier rings coated with a culture of methanotropic bacteria and kaolin clay, wherein the kaolin clay is coated on the carrier rings from a salts solution having a kaolin clay concentration of 0.004% to 4% w/v;

b. a conduit connecting a bioreactor container outlet to a gas pump;

c. a second conduit connecting the gas pump to a lower part of the bioreactor container;

d. a gas sample valve connecting to the second conduit means; and e. a humidifying salt solution within the lower part of the bioreactor container, wherein the gas is circulated through the salt solution and carrier means by the gas pump so as to remove the methane vapor from the gas.

* * * * *